(12) United States Patent
Cashman et al.

(10) Patent No.: US 6,585,727 B1
(45) Date of Patent: Jul. 1, 2003

(54) SURGICAL INSTRUMENT LIGHT SOURCE AND SURGICAL ILLUMINATION METHOD

(75) Inventors: Christopher M. Cashman, Alpharetta, GA (US); Keith Wells, Marietta, GA (US)

(73) Assignee: Genzyme Corporation, Cambridge, MA (US)

( * ) Notice: Subject to any disclaimer, the term of this patent is extended or adjusted under 35 U.S.C. 154(b) by 151 days.

(21) Appl. No.: 09/691,902

(22) Filed: Oct. 19, 2000

Related U.S. Application Data
(60) Provisional application No. 60/160,987, filed on Oct. 22, 1999.

(51) Int. Cl.⁷ .................................................. A61B 1/06
(52) U.S. Cl. ........................................................ 606/16
(58) Field of Search ................................. 606/174, 159; 158/20; 362/31, 32, 804; 350/96.1; 600/201, 104, 210, 310; 52/301; D26/27; 40/547

(56) References Cited

U.S. PATENT DOCUMENTS

| | | | |
|---|---|---|---|
| 4,052,980 A | | 10/1977 | Grams et al. |
| 4,562,832 A | * | 1/1986 | Wilder et al. |
| 4,597,030 A | | 6/1986 | Brody et al. |
| 4,759,348 A | * | 7/1988 | Cawood |
| 4,765,701 A | | 8/1988 | Cheslak |
| 4,996,976 A | | 3/1991 | Nakagawa |
| 5,005,108 A | | 4/1991 | Pristash et al. |
| 5,035,232 A | | 7/1991 | Lutze et al. |
| 5,450,293 A | * | 9/1995 | Hoffman |
| 5,503,617 A | | 4/1996 | Jako |
| 5,514,076 A | | 5/1996 | Ley |
| 5,514,077 A | | 5/1996 | Rabban |
| 5,667,480 A | | 9/1997 | Knight et al. |
| 5,722,934 A | | 3/1998 | Knight et al. |
| 5,725,479 A | | 3/1998 | Knight et al. |
| 5,730,748 A | | 3/1998 | Fogarty et al. |
| 5,776,159 A | | 7/1998 | Young |
| 5,797,947 A | | 8/1998 | Mollenauer |
| 5,827,318 A | | 10/1998 | Bonutti |
| 5,853,417 A | | 12/1998 | Fogarty et al. |
| 5,904,650 A | | 5/1999 | Wells |
| 5,913,818 A | | 6/1999 | Co et al. |
| 5,921,919 A | | 7/1999 | Chin et al. |
| 5,928,137 A | * | 7/1999 | Green |
| 5,967,971 A | | 10/1999 | Bolser |
| 6,033,361 A | | 3/2000 | Co et al. |

FOREIGN PATENT DOCUMENTS

WO    WO 99/01696    1/1999

OTHER PUBLICATIONS

Auto Suture Company, The Mini–Harvest System for Minimally Invasive Saphenous Vein Harvesting, 1996.

Design News, Medical Plastic/Cover Story, Bypas Surgery Made Easier, Disposable Instruments, made from standard plastics, key to minimally invasive procedure for extracting veins, Gary Chamberlain, Senior Editor, pp. 57–58; 60, 62 (Jan. 6, 1997).

(List continued on next page.)

Primary Examiner—Ismael Izaguirre
(74) Attorney, Agent, or Firm—Richard D. Allison; Thomas J. DesRosier

(57) ABSTRACT

A fiber optic cable to be used with surgical instruments is provided wherein the cable is temporarily attached to the surgical instrument with which it is used, and mounted in an open design to allow illumination to a wider portion of the targeted area such that an entire surgical pocket may be illuminated, and the cables provided can be disposable without requiring permanent attachment to an instrument or development of surgical instruments permanently incorporating a light source by providing a plurality of guide members on the surgical instrument so the cable may be threaded through the guides and preferably engaged by at least one of the guides.

20 Claims, 6 Drawing Sheets

OTHER PUBLICATIONS

Dimitri, W. R. et al., A Quick and Atraumatic Method of Autologous Vein Harvesting Using the Subcutaneous Extraluminal Dissector, J. Cardiovasc. Surg., vol. 28, pp. 103–111 (1987).

Dregelid, E. et al., Endothelial Cell Injury in Human Saphenous Veins After Manipulation and Tweezer Grasping, J. Cardiovasc. Surg., vol. 29, pp. 464–469 (1988).

Gundry, Steven R., et al., Optimal Preparation Techniques for Human Saphenous Vein Grafts, Surgery, No. 6, pp. 785–794 (Dec. 1980).

Hauer, G. et al., Endoscopic Subfascial Discission of Perforating Veins, Surg. Endosc., vol. 2, pp. 5–12 (1988).

Lee, John, Surgical Physician Assistant, Minimally Invasive Vein Harvesting, Nov./Dec. 1996, pp. 26–32.

Meldrum–Hanna, W. et al., Long Saphenous Vein Harvesting, Aust. N.Z. J. Surg., vol. 56, pp. 923–924 (1986).

Moazami, Nader et al., Minimally Invasive Greater Saphenous Vein Harvesting for Coronary Artery Bypass Surgery, Surgical Rounds, pp. 94–97 (Mar. 1997).

Rashid, A. et al., Subcutaneous Technique for Saphenous Vein Harvest, The Annals of Thoracic Surgery, vol. 37, No. 2, pp. 169–170 IFeb. 1984).

Snowden Pencer DSP, The Diamond–Line of Surgical Instruments Brochure, Tebbets EndoPlastic Instrument System, 1995.

Snowden Pencer DSP, EndoCABG System, Innovative Instrumentation for Endoscopic Coronary Artery Bypass Grafting, 1996.

Wheatley, D.J.,Autocronary Bypass Grafting Techniques, Surgery of Coronary Artery Disease, pp. 348–349 (Date Unknown).

* cited by examiner

US 6,585,727 B1

SURGICAL INSTRUMENT LIGHT SOURCE AND SURGICAL ILLUMINATION METHOD

This application claims the benefit of Provisional Application No. 60/160,987, filed Oct. 22, 1999.

BACKGROUND OF THE INVENTION

Light sources for use with surgical instruments and lighting techniques for medical procedures are known in the art. Existing surgical light sources involve fiber optic bundles permanently attached to a particular surgical instrument. These bundles are typically attached to the instrument by means of a rigid stainless steel tube brazed to the instrument. These light sources are limited in flexibility by the fiber optic bundles, and limited by a closed design that provides illumination to only the small, targeted area.

The present invention provides a single-strand fiber optic cable to be used with surgical instruments. This minute cable is only temporarily attached to the surgical instrument with which it is used, and mounted in an open design to allow illumination to a wider portion of the targeted area. As a result, an entire surgical pocket may be illuminated, and the cables provided can be disposable without requiring permanent attachment to an instrument or development of surgical instruments permanently incorporating a light source.

1. Field of the Invention

This invention pertains to medical instruments, and more particularly to apparatus for illuminating body areas undergoing surgery.

2. Description of the Prior Art

It is imperative that adequate lighting be provided to affected regions during surgical procedures. However, overhead room lighting is rarely sufficient for operating purposes. Accordingly, various types of supplemental lighting equipment have been developed that suits different medical illumination requirements.

For example, surgical retractors useful in oral surgery include a fiber optic cable. The fiber optic cable is clipped to an external surface of the retractor. One end of the fiber optic cable is connected to a source of illumination. The output end of the fiber optic cable is positioned to direct a focused beam of light on the mouth area being treated. Although useful, the externally clipped fiber optic cable is prone to being bumped and misdirected during use. Furthermore, if debris obstructs the end of the cable, the illumination is blocked. Another use of fiber optic illumination includes a headlight lighting system wherein the output end of a fiber optic cable is connected to a headband worn by a surgeon. The fiber optic cable supplies light to a headlight on the headband. The headlight may be fixed or moveable to suit different requirements. By moving his head and/or the headlight, the surgeon is able to direct light to the region where he is working. Clipping a fiber optic cable onto the retractor in the manner of orthodontic instruments is not an acceptable solution, because of the potential for the fiber optic cable to be bumped or dislodged. In addition, the prior fiber optic cable design would decrease the volume within the cavity that is available to the surgeon's fingers and instruments. Another drawback of the prior fiber optic cable and clip combination is that the loss of light from a small spatter of blood or other fluid on the output end of the fiber optic cable would be intolerable. Thus, a need exists for an improved surgical lighting system.

SUMMARY OF THE INVENTION

In accordance with the present invention, an illuminated instrument is provided that greatly increases the illumination. In a preferred form of the present invention, a plurality of connectors are attached to the instrument and the fiber optic cable is threaded through at least one of the connectors to hold the fiber optic cable immediately adjacent to the side of the instrument. The fiber optic cable preferably is partially shielded along the length thereof and the distal end portion is preferably unshielded so that the illumination extends lengthwise along the desired portion of the instrument and may additionally be directed forwardly thereof to provide the desired illumination characteristics for the instrument and procedure. An additional feature of the present invention is that the fiber optic cable may be used for multiple procedures so that as the fiber optic cable becomes worn or frayed, the cable may be cut and then the shielding may be removed from the desired portion of the cable. The fiber optic cable is then reinstalled on the instrument.

DETAILED DESCRIPTION OF THE INVENTION

Because of the nature of surgical procedures, light sources and methods of illumination provide advantages to the operating physician. The limited maneuverability within a surgical area or surgical pocket, however, restricts the size of instruments and light sources that can be used to illuminate the targeted area.

The present invention provides for a light source that may be temporarily and securely attached to a scissor, retractor, forceps, electrode or similar surgical instrument. A conventional single fiber optic cable 10 is connected to a commercially available light source such as a 300 watt light source, or other similar medical light providing source well-known in the art. The fiber optic cable 10 preferably includes a shielded outer surface 12 that extends lengthwise along the fiber optic cable 10. At least a segment of the fiber optic cable and preferably including the distal end portion 14 of the fiber optic cable 10 is exposed to allow the light energy to be released from the exposed surface. It is anticipated that the shielded outer surface of the fiber optic cable may be removed along the entire distal end portion 12 or be selectively removed from a segment or side surface of the fiber optic cable to enable the illumination of a desired portion of the surgical site while, preferably not shining back into the user's eyes.

Figure 1A:
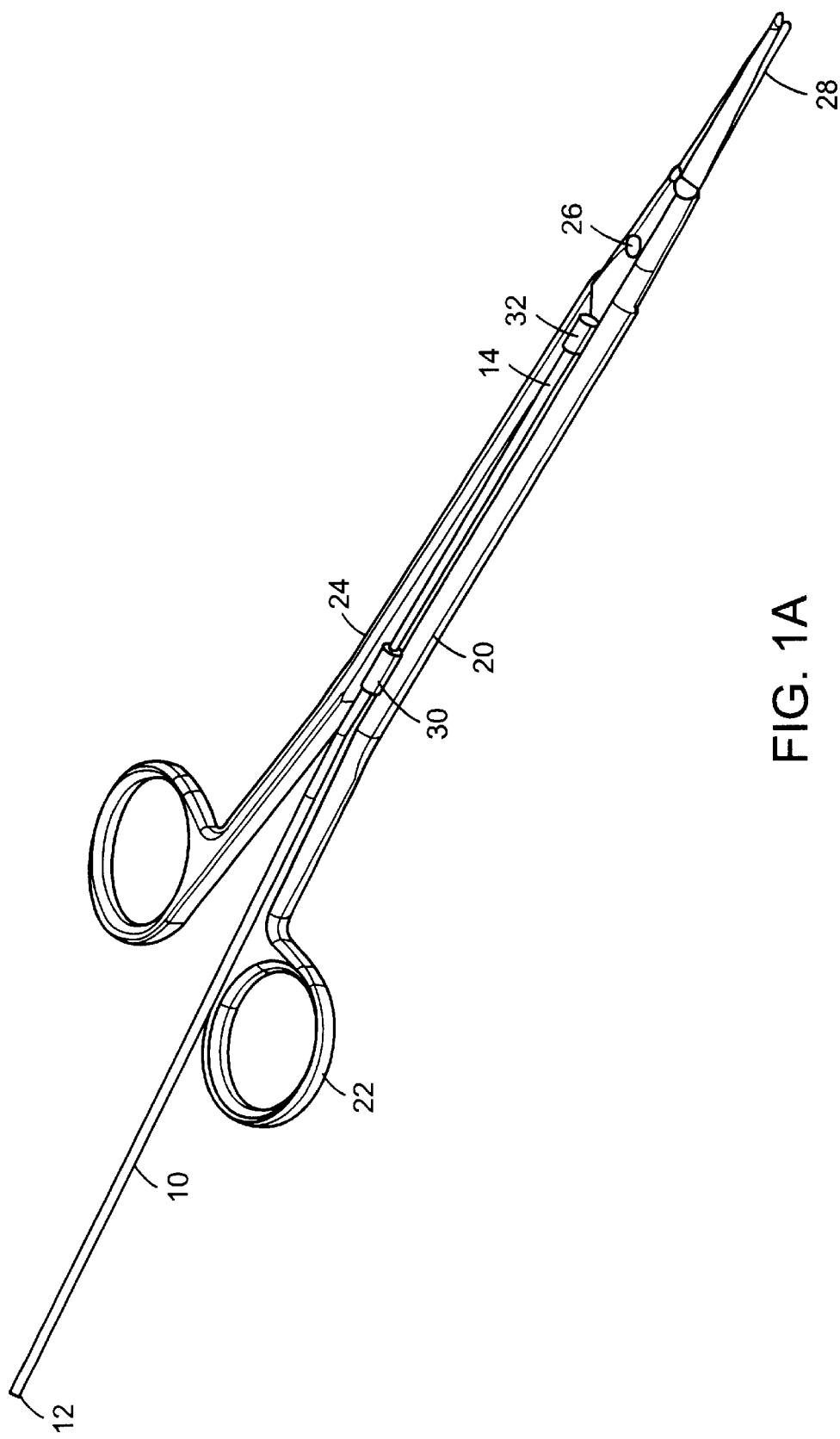
FIG. 1A is a perspective view of the scissor embodiment of the present invention.
Figure 1B:
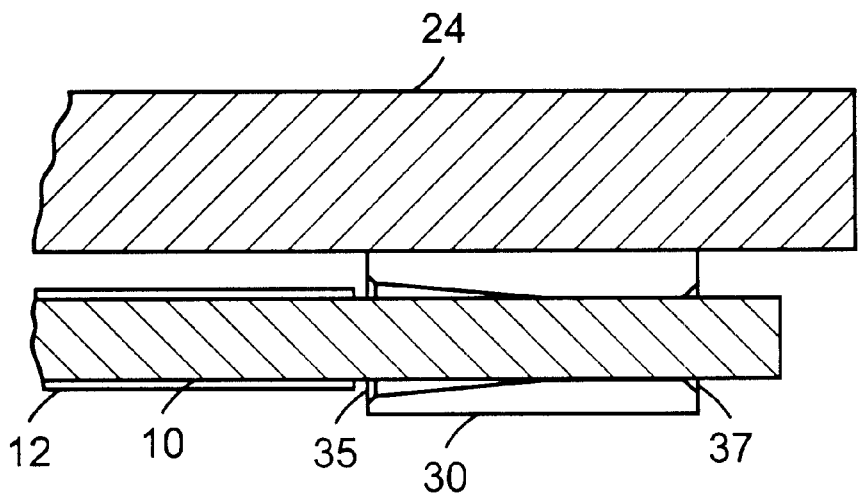
FIG. 1B is a cross-sectional view of the first connector of the first guide of the present invention.
Figure 1C:
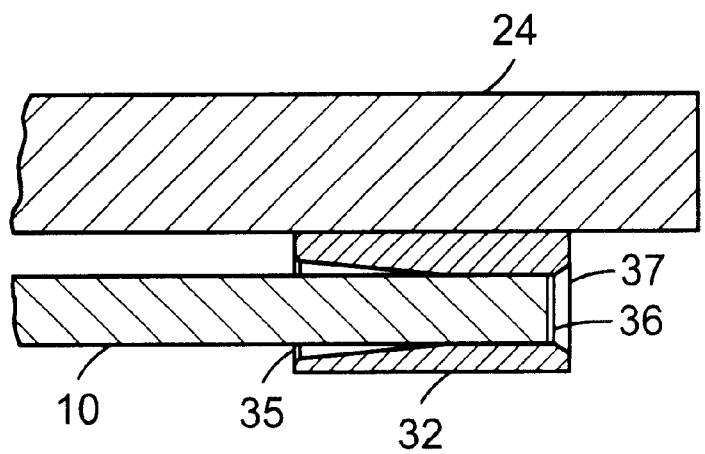
FIG. 1C is a cross-sectional view of the first connector of the second guide of the present invention

As shown in FIGS. 1A–1C, the present invention may include an illuminated scissor instrument 20. The scissor 20 includes a pair of finger rings 22 on the proximal end thereof with the corresponding handle portions 24 extending distally therefrom to the pivot 26. The cutting blades 28 are located distally thereof and may be straight, as shown, or may include complementarily curved cutting surfaces. One or more small hollow cylindrical guides 30 and 32 are preferably affixed to one of the handle portions 24. The guides may be affixed in a conventional manner using adhesives or by being soldered to the handle portion 24 of a surgical instrument, such as the scissors shown in the drawings. In the preferred form of the present invention, the guides, 30 and 32, are open at each end. As shown in FIG. 1B, the cable is threaded through the first guide 30 such that the fiber optic cable enters through a tapered opening 33 and passes therethrough to the second guide 32. The second guide is shown in FIG. 1C and preferably includes the tapered opening 35 and the securing stop 36. Additionally, as shown, the distal side 37 of the second guide 32 is open to allow illumination from the fiber optic cable to pass therethrough. The single fiber optic cable 10 is threaded through the guides 30 and 32 along the scissor instrument 20 such that the side profile thereof is not substantially altered. The guides 30 and 32 are spaced apart along the instrument such that the threaded cable 10 is exposed between the guides. The second guide 32 on the instrument includes the small securing stop 36 to securely hold and retain the distal end portion 12 of the single fiber optic cable in the desired position along the handle portion of the scissor. Preferably the securing stop 36 is a small crimp or similar interference located generally adjacent to the pivot. In the preferred embodiment, the portion of the single fiber optic cable that is threaded between the guides 30 and 32 is unshielded to allow illumination to pass therefrom. For example, in this embodiment, the distal end portion 14 includes a small amount (about the last ⅛ inch) of the single fiber optic cable that is held by the crimp and securing stop 32. It is also anticipated that an additional guide may be used in this embodiment, for example, on one of the finger rings 22 or along the handle portion, to further secure the fiber optic cable in a low profile and secure manner along the length of the scissor instrument.

Because the fiber optic cable is preferably unshielded and exposed between the guides 30 and 32, light through the fiber optic cable from the light source, can illuminate both from along the walls of the fiber optic cable and out the end of the cable through the distal side 37 of the second guide 32. Consequently, an entire surgical pocket rather than only a spot target area at the end of the surgical instrument light source can be lighted during the surgical procedure. Further, because the cable is a single fiber, rather than bundles, enhanced flexibility of the light source and surgical instrument is provided.

Another advantage of the present invention is the temporary attachment of the fiber optic cable. The fiber optic cable threads freely and easily through the hollow cylindrical guides on the scissor instrument. Reverse pulling pressure can easily free the fiber optic cable from the securing stop. The fiber optic cable is thus disposable, and can be easily replaced by another cable, or by cutting off the end of used cable, and threading unused cable forward into the guides. The temporary attachment and disposable fiber optic cable provides advantages over permanent surgical instrument light sources in both cleaning, cost of manufacture, and efficiency. The illuminated instrument of the present invention renders the surgical field well lit during operations while remaining unobstructive to the surgeon. This desirable result comes from using the combined functions of fiber optic cable and the profile of the illuminated instrument. The illuminated instrument can be made in different sizes to suit different patients. The location of the fiber optic cable output end can also be varied to suit different applications such that the distal end portion of the fiber optic cable may be oriented to extend distally beyond the guide 32 and pivot to a location that is generally adjacent to the cutting surface of the scissor instrument.

Figure 2:
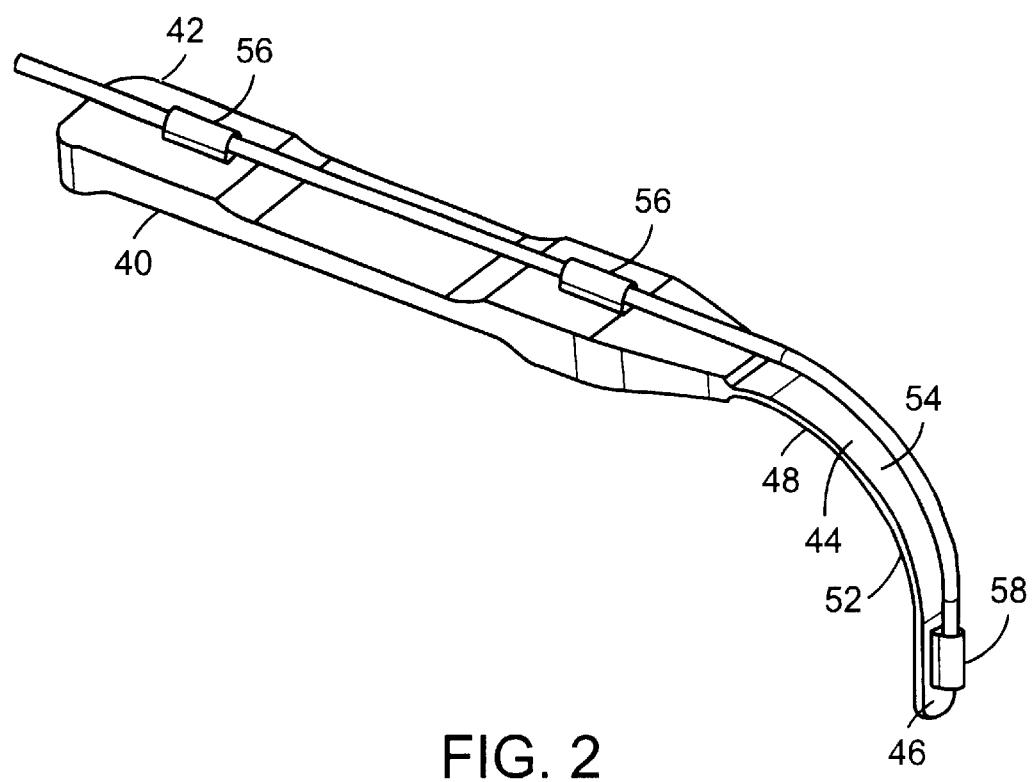
FIG. 2 is a perspective view of a retractor embodiment of the present invention.

As shown in FIG. 2, the present invention may also include an illuminated retractor instrument 40. The retractor includes an elongate handle section 42 on the proximal end thereof with the blade shaped section 44 extending distally therefrom. The blade section 44, in this embodiment, includes a plurality of surfaces that are located distally of the handle section and may include tapered or gradually curved surfaces, as shown, or may be straight that lead to a generally flat surface 46 that is oriented generally perpendicular or at an acute angle with respect to the handle section 42. As shown, the blade section 44 includes a curved surface 48 that extends between the handle section 42 and the flat surface 46. The flat surface is also preferably oriented generally perpendicular to the handle section 42. The flat surface 46 is preferably generally flat in the lengthwise dimension and may have a slight curve along the width of the surface. Additionally, the flat surface 46 preferably includes an inner surface 52 and an outer surface 54. The inner surface may have a slightly convex surface and the outer surface preferably has a slightly concave surface.

The handle section 42 of this embodiment preferably includes a pair of connectors 56 thereon. This connectors 56 are preferably located near the proximal and distal end portions of the handle section and include an elongate and tubular member that slidably receives the fiber optic cable therethrough to retain the fiber optic cable adjacent to the handle section 42. A further connector 58 is provided on the outer surface 54 of the flat surface 46 of the blade section. This connector 58 preferably frictionally engages the distal end portion of the fiber optic cable to retain the fiber optic cable in the desired position adjacent the flat surface 46. Additionally, in this embodiment, the connector 58 may be a clip type of connector such that the distal end portion of the fiber optic cable may be positioned under the connector while allowing light to pass from the distal end of the fiber optic cable. Additionally, this connector 58 preferably provides sufficient resistance to the movement of the fiber optic cable so that the remaining portion of the fiber optic cable between the connectors 56 and 58 may be pulled taut so as to be positioned adjacent to the outer surface of each portion of the blade section such that the profile thereof is not substantially altered. Furthermore, the distal end portion of the connector 58 is preferably open to allow illumination from the fiber optic cable to pass therefrom forwardly of the distal end portion of the flat surface of the blade section.

In use, a desired amount of the sheath of the distal end portion of the fiber optic cable is removed and the fiber optic cable 10 is threaded through the first connectors 56. Next the distal end portion of the fiber optic cable is positioned to be engaged by the second connector 58. The length of the fiber optic cable is then pulled proximally until the fiber optic cable is positioned adjacent to the outer surface of the blade section. As the retractor is used to retract the desired tissue, light is illuminated from the unsheathed portion of the fiber optic cable to illuminate the surgical site. Once the procedure is completed, the fiber optic cable may be withdrawn from the retractor by releasing the fiber optic cable from the connector 58 and then unthreading the fiber optic cable from connectors 56. Thereafter, the retractor may be sterilized in preparation for the next use and the fiber optic cable may be cleaned or replaced prior to the next use as desired.

Figure 3A:
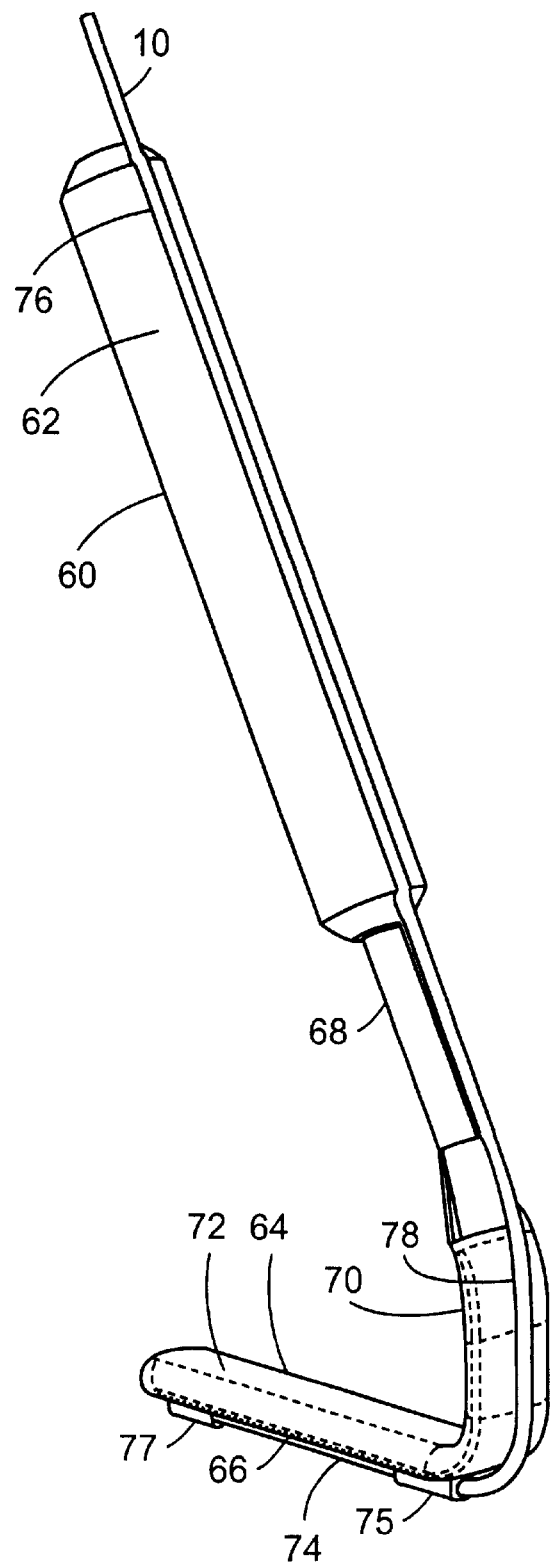
FIGS. 3A is a perspective view of a further retractor embodiment of the present invention.
Figure 3B:
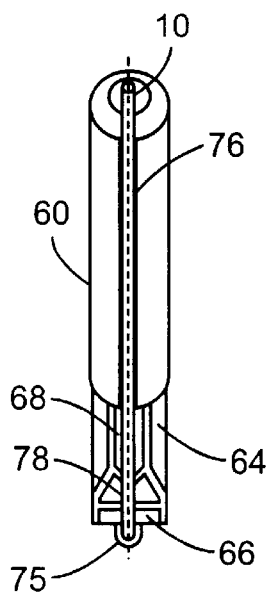
FIG. 3B is a top perspective view of the retractor of FIG. 3A.
Figure 3C:
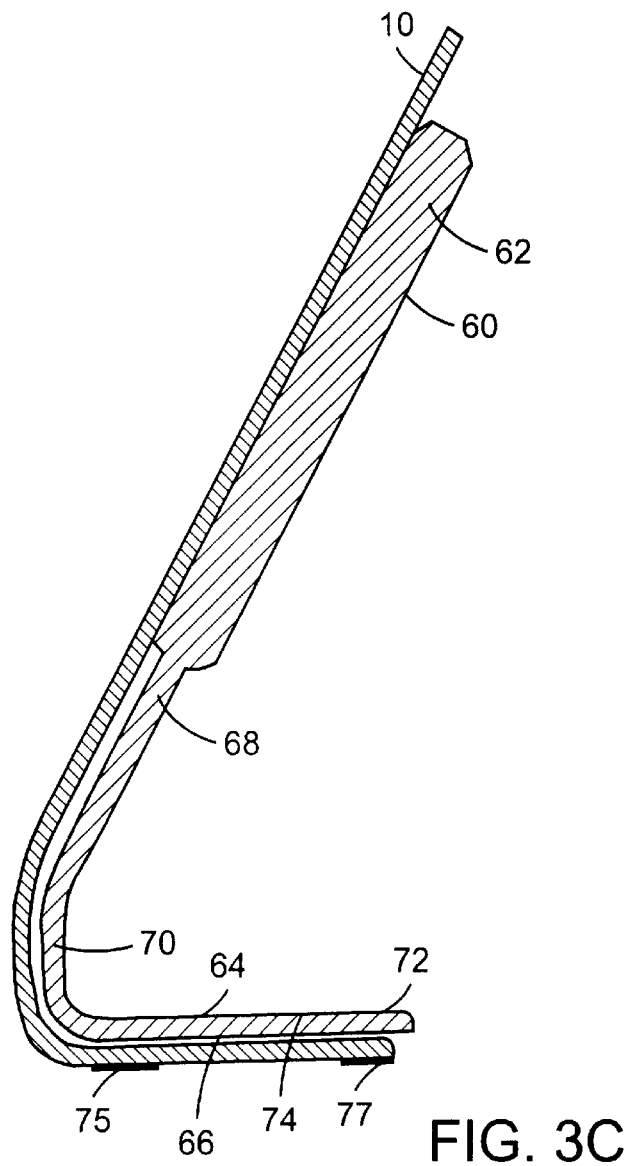
FIG. 3C is a cross-sectional view of the retractor of FIG. 3A.

As shown in FIGS. 3A–3C, the present invention may also include an illuminated retractor instrument 60. The retractor includes an elongate handle section 62 on the proximal end thereof with the blade shaped section 64 extending distally therefrom. The blade section 64, in this embodiment, includes a plurality of surfaces that are located distally of the handle section and may include straight, tapered or gradually curved surfaces that lead to a generally flat surface 66 that is oriented generally perpendicular or at an acute angle with respect to the handle portion. As shown, the blade section 64 includes a first surface 68 that is generally parallel to the handle section 62 and a second surface 70 that extends distally from the first surface 68 and is oriented at a slight angle thereto. The second surface 70 is also oriented generally perpendicular to the flat surface 66. The flat surface 66 is preferably generally flat in the lengthwise dimension and may have a slight curve along the width of the surface. Additionally, the flat surface 66 preferably includes an inner surface 72 and an outer surface 74. The inner surface preferably has a slightly convex surface and the outer surface preferably has a slightly concave surface to assist in retaining and supporting the tissue that is to be retracted by the retractor.

The handle section 62 of this embodiment preferably includes at least one elongate channel 76 extending lengthwise therealong. This channel 76 is preferably located along the outer surface of the handle section and is sufficiently wide and deep to receive the fiber optic cable therein to retain the fiber optic cable adjacent to the handle section 62 in use. A further channel 78 is preferably provided on the outer surface of the second surface 70 of the blade section. This channel 78 preferably receives the flexible fiber optic cable therein to retain the fiber optic cable in the desired position adjacent the flat surface 66.

The blade section 64 of this embodiment preferably includes a pair of connectors 75 and 77 thereon. This connectors 75 and 77 are preferably located near the proximal and distal end portions of the blade section. The connector 75 preferably includes an elongate and tubular member that slidably receives the fiber optic cable therethrough to retain the fiber optic cable adjacent to the proximal end portion of the blade section. The second connector 77 is provided on the outer surface 74 of the flat surface 66 of the blade section 64. This connector 77 preferably frictionally engages the distal end portion of the fiber optic cable to retain the fiber optic cable in the desired position adjacent the flat surface 66. Additionally, in this embodiment, the connector 77 may be a clip type of connector such that the distal end portion of the fiber optic cable may be positioned under the connector while allowing light to pass from the distal end of the fiber optic cable. Additionally, this connector 77 preferably provides sufficient resistance to the movement of the fiber optic cable so that the remaining portion of the fiber optic cable between the connector 75 and the channels may be pulled taut so as to be positioned in the channels and adjacent to the outer surface of each portion of the blade section such that the profile thereof is not substantially altered. Furthermore, the distal end portion of the connector 77 is preferably open to allow illumination from the end thereof to shine forwardly of the distal end portion of the retractor.

In use, a desired amount of the sheath of the distal end portion of the fiber optic cable is removed and the fiber optic cable 10 is positioned in the channels and then threaded through the first connector 75. Next the distal end portion of the fiber optic cable is positioned to be engaged by the second connector 77. The length of the fiber optic cable is then pulled proximally until the fiber optic cable is positioned in the respective channels, around the curve and adjacent to the outer surface of the blade section. As the retractor is used to retract the desired tissue, light is illuminated from the unsheathed portion of the fiber optic cable to illuminate the surgical site. Once the procedure is completed, the fiber optic cable may be withdrawn from the retractor by pulling the fiber optic cable with a proximally directed force and releasing the fiber optic cable from the connector 77 and then unthreading the fiber optic cable from connector 75 and removing the fiber optic cable from the channels. Thereafter, the retractor may be sterilized in preparation for the next use and the fiber optic cable may be cleaned or replaced prior to the next use as desired.

Figure 4:
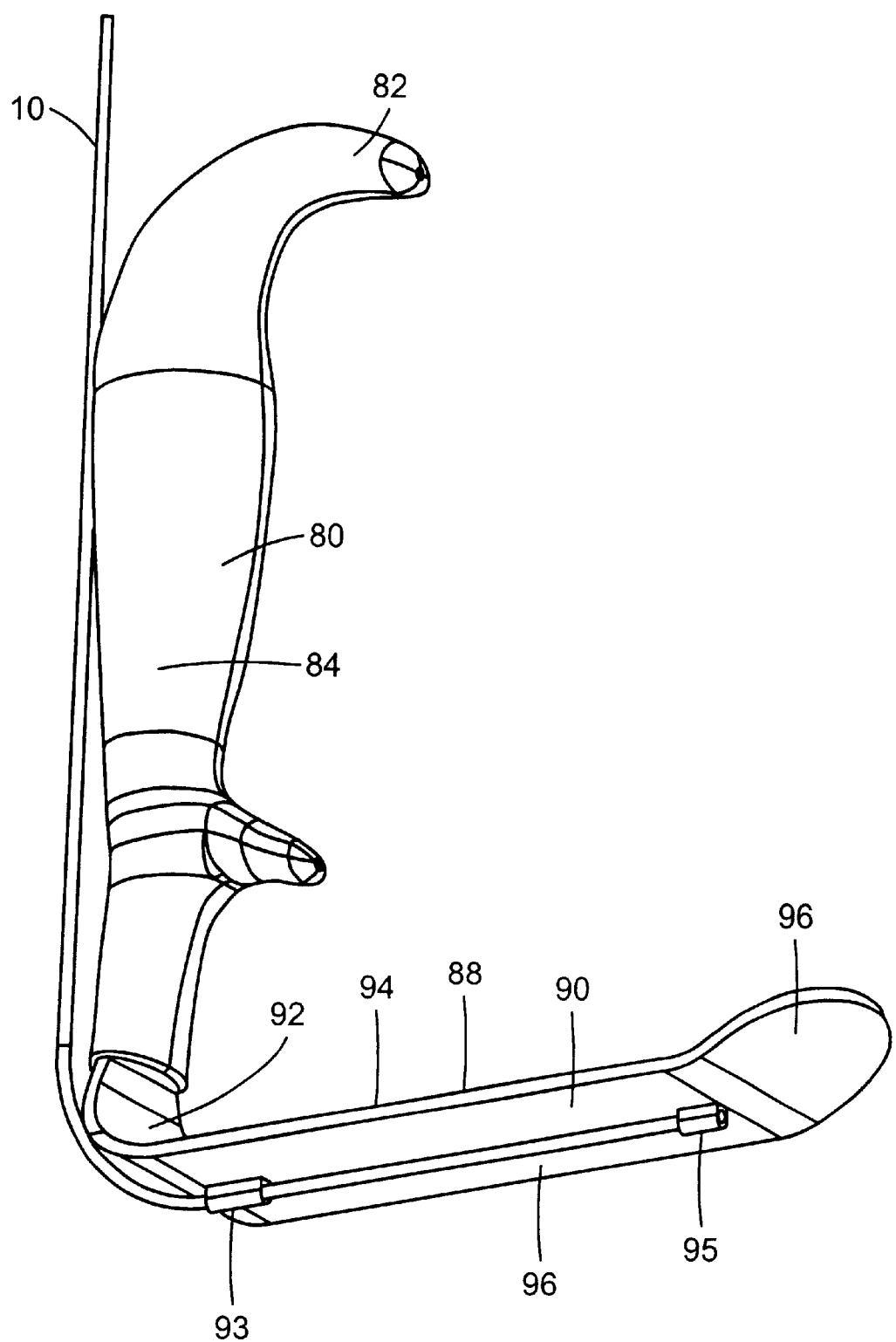
FIG. 4 is a perspective view of a further retractor embodiment of the present invention.

As shown in FIG. 4, the present invention may also include a Tebbetts type of illuminated retractor instrument 80 as shown in the drawings. The retractor includes a curved proximal end portion 82 with an elongate handle section 84 having various finger grip members thereon and the blade shaped section 88 extending distally therefrom. The curved proximal end portion 82 of the retractor is preferably shaped to assist the user in grasping the retractor and while also providing a surface for attachment to a mechanical support device, such as those used during various surgeries that are attached to the patient's bedside or a chest spreader or similar tissue spreading device.

The blade section 88, in this embodiment, includes a plurality of surfaces that are located distally of the handle section and may be straight and relatively flat, as shown, or may include tapered or gradually curved surfaces that lead to or extend from the wider and generally flat surface 90 that is oriented generally perpendicular or at an acute angle with respect to the handle portion. As shown, the blade section 88 includes a first surface 92 that is curved between to the handle section 84 and the flat surface 90. The flat surface 88 is preferably generally flat in the lengthwise dimension and may have a slight curve along the width of the surface. Additionally, the flat surface 88 preferably includes an inner surface 94 and an outer surface 96. The inner surface preferably has a slightly convex surface and the outer surface preferably has a slightly concave surface and is preferably formed of a reflective material to assist in the dissemination of the light engery from the fiber optic cable. The distal end portion for the flat surface 88 preferably includes an upwardly extending tip member 96 that includes a curved end portion.

In this embodiment, the first surface 92 of the blade section 88 preferably includes at least one connector 93 thereon. This connector 93 is preferably located lengthwise along the outer surface of the first surface and extends from a location near the proximal end portion of the flat surface. The connector 93 preferably includes an elongate an tubular member that is positioned adjacent the curve formed by the intersection of the first surface and the flat surface and which slidably receives the fiber optic cable therethrough to retain the fiber optic cable adjacent to the blade section 88. It is anticipated that a further connector or a channel may be provided adjacent to the proximal end portion of the handle section to ensure that the fiber optic cable is adjacent to the handle section and does not interfere with the use of the retractor.

A further connector 95 is provided on the outer surface of the flat surface of the blade section adjacent to the distal end portion thereof. This connector 95 preferably frictionally engages the distal end portion of the fiber optic cable to retain the fiber optic cable in the desired position adjacent the flat surface. Additionally, in this embodiment, the connector 95 may be a clip type of connector (not shown) such that the distal end portion of the fiber optic cable may be positioned under the connector while allowing the distal end portion of the fiber optic cable to extend therefrom. Additionally, this connector 95 preferably provides sufficient resistance to the movement of the fiber optic cable so that the portion of the fiber optic cable between the connectors 93 and 95 may be pulled taut so as to be positioned adjacent to the outer surface of each portion of the blade section such that the profile thereof is not substantially altered.

In use, a desired amount of the sheath of the distal end portion of the fiber optic cable is removed and the fiber optic cable 10 is threaded through the first connector 93. Next the distal end portion of the fiber optic cable is positioned to be engaged by the second connector 95. In this embodiment, the user may determine the amount of fiber optic cable, if any, that is desired to extend distally beyond the connector 93 as the fiber optic cable is installed on the retractor and the illumination is present primarily from the flat surface of the retractor. The length of the fiber optic cable is then pulled proximally until the fiber optic cable is positioned adjacent to the outer surface of the blade section. As the retractor is used to retract the desired tissue, the user may grasp the fiber optic cable adjacent to the handle section and light is illuminated from the unsheathed portion of the fiber optic cable to illuminate the surgical site. Once the procedure is completed, the fiber optic cable may be withdrawn from the retractor by releasing the fiber optic cable from the connector 95 and then unthreading the fiber optic cable from connector 93. Thereafter, the retractor may be sterilized in preparation for the next use and the fiber optic cable may be cleaned or replaced prior to the next use as desired.

While the invention has been described with reference to the structure and methods disclosed, it is not confined to the details set forth, but is intended to cover such modifications or changes as may fall within the scope of the following claims.

What is claimed is:

1. A medical device including a light source for illuminating a surgical site during surgical procedures comprising:
    a. an elongate surgical instrument;
    b. a plurality of guides fixedly connected lengthwise along the surgical instrument;
    c. a flexible fiber light cable threaded through the guides, wherein said cable has a surface between the guides for providing illumination therefrom to the surgical site;
    d. a securing stop in a last guide that removably secures the light cable at one end portion of the cable; and
    e. a light source connected to the end of the cable opposite the end of the cable secured in the securing stop.

2. The medical device of claim 1 wherein said plurality of guides includes a proximal guide and a distal guide and said distal guide includes said securing stop therein to frictionally retain said light cable therein.

3. A medical device including a light source for illuminating surgical procedures comprising:
    a. an elongate surgical instrument;
    b. a plurality of guides fixedly connected lengthwise along the surgical instrument;
    c. a flexible fiber light cable threaded through the guides, wherein said cable has an exposed surface between the guides for illuminating through said exposed surface;
    d. a securing stop in a last guide that removably secures the light cable a one end portion of the cable;
    e. a light source connected to the end of the cable opposite the end of the cable seured in the securing stop;
    f. wherein said plurality of guides includes a proximal guide and a distal guide and said distal guide includes said securing stop therein to frictionally retain said light cable therein; and
    g. wherein said proximal guide movably retains said cable adjacent to at least a portion of the surgical instrument.

4. A medical device including a light source for illuminating surgical procedures comprising:
    a. an elongate surgical instrument;
    b. a plurality of guides fixedly connected lengthwise along the surgical instrument;
    c. a flexible fiber light cable threaded through the guides, wherein said cable has an exposed surface between the guides for illuminating through said exposed surface;
    d. a securing stop in a last guide that removably secures the light cable at one end portion of the cable;
    e. a light source connected to the end of the cable opposite the end of the cable secured in the securing stop; and
    f. wherein said cable includes an outer shielding thereon to obstruct illumination from passing therefrom and said shielding is removed therefrom along the portion of the cable that is exposed between the plurality of guides to enable illumination to pass therefrom.

5. A medical device including a light source for illuminating a surgical site during surgical procedures comprising:
    a. an elongate surgical instrument;
    b. a plurality of guides fixedly connected lengthwise along the surgical instrument;
    c. a flexible fiber light cable threaded through the guides, wherein said cable is retained between the guides and includes a surface thereon for providing illumination therefrom to the surgical site;
    d. a securing stop in a last guide that removably secures the light cable at one end portion of the cable;
    e. a light source connected to the end of the cable opposite the end of the cable secured in the securing stop; and
    f. wherein the cable is aligned along the lengthwise dimension of the surgical instrument when the cable is threaded through the plurality of guides and wherein the cable is removable from the guides upon the application of a proximally directed force to the cable.

6. The medical device of claim 5 wherein the surgical instrument is a scissor.

7. The medical device of claim 5 wherein the surgical instrument is a retractor.

8. The medical device of claim 5 wherein the surgical instrument is a curved instrument and the cable is threaded along the curvature of the surgical instrument.

9. The medical device of claim 8 wherein the surgical instrument includes a handle portion and a blade section wherein the cable is threaded therealong and the blade section includes a guide thereon that frictionally engages the cable.

10. A medical device including a light source for illuminating surgical procedures comprising:
    a. an elongate surgical instrument;
    b. a plurality of guides fixedly connected lengthwise along the surgical instrument;
    c. a flexible fiber light cable threaded through the guides, wherein said cable has an exposed surface between the guides for illuminating through said exposed surface;
    d. a securing stop in a last guide that removably secures the light cable at one end portion of the cable;

e. a light source connected to the end of the cable opposite the end of the cable secured in the securing stop; and f. wherein the cable is removable from the guides upon the application of a proximally directed force to the cable.

11. A medical device including a light source for illuminating a surgical site during surgical procedures comprising:

an elongate surgical instrument having a distal end portion and a proximal end portion;

a plurality of guides fixedly connected lengthwise along the surgical instrument;

a flexible fiber light cable associated with the guides and oriented to extend substantially lengthwise along the surgical instrument and wherein said cable has an illumination surface between the guides for providing illumination to the surgical site from said illumination surface;

a securing stop in at least one guide to frictionally secure the light cable to said at least one guide at one end portion of the cable; and a light source connected to the end portion of the cable opposite the end of the cable secured in the securing stop.

12. The medical device of claim 11 wherein said cable includes at least a portion thereof that provides illumination forwardly thereof.

13. The medical device of claim 11 wherein the surgical instrument includes a curved portion and the cable is threaded therearound between the guides.

14. A medical device including a light source for illuminating surgical procedures comprising:

an elongate surgical instrument having a distal end portion and a proximal end portion;

a plurality of guides fixedly connected lengthwise along the surgical instrument;

a flexible fiber light cable associated with the guides and oriented to extend substantially lengthwise along the surgical instrument and wherein said cable has an exposed surface between the guides for providing illumination through said exposed surface;

a securing stop in at least one guide to frictionally secure the light cable to said at least one guide at one end portion of the cable;

a light source connected to the end portion of the cable opposite the end of the cable secured in the securing stop; and wherein the securing stop is a clip member that frictionally and releasably engages the cable to align the cable along the lengthwise dimension of the surgical instrument.

15. A medical device including a light source for illuminating surgical procedures comprising:

an elongate surgical instrument having a distal end portion and a proximal end portion;

a plurality of guides fixedly connected lengthwise along the surgical instrument;

a flexible fiber light cable associated with the guides and oriented to extend substantially lengthwise along the surgical instrument and wherein said cable has an exposed surface between the guides for providing illumination through said exposed surface;

a securing stop in at least one guide to frictionally secure the light cable to said at least one guide at one end portion of the cable;

a light source connected to the end portion of the cable opposite the end of the cable secured in the securing stop; and wherein the surgical instrument includes a handle portion and a blade section and the handle portion includes a first guide thereon and the blade section includes a second guide thereon and wherein the cable is slidable through the first guide and engaged by the second guide.

16. The medical device of claim 15 wherein the cable is releasable from said second guide upon the application of a proximally directed force thereto.

17. The medical device of claim 15 wherein said handle portion is oriented at a generally perpendicular angle with respect to the blade section.

18. The medical device of claim 15 wherein the handle portion is generally circular in cross section and said blade section is generally flat in cross section.

19. A medical device including a light source for illuminating surgical procedures comprising:

an elongate surgical instrument having a distal end portion and a proximal end portion;

a plurality of guides fixedly connected lengthwise along the surgical instrument;

a flexible fiber light cable associated with the guides and oriented to extend substantially lengthwise along the surgical instrument and wherein said cable has an exposed surface between the guides for providing illumination through said exposed surface;

a securing stop in at least one guide to frictionally secure the light cable to said at least one guide at one end portion of the cable;

a light source connected to the end portion of the cable opposite the end of the cable secured in the securing stop; and including first and second guides thereon wherein the cable is slidable through the first guide and is releasably engaged by the second guide.

20. A medical device including a light source for illuminating surgical procedures comprising:

an elongate surgical instrument having a distal end portion and a proximal end portion;

a plurality of guides fixedly connected lengthwise along the surgical instrument wherein a first guide is generally associated with the proximal end portion and a second guide is generally associated with the distal end portion;

a flexible fiber light cable associated with the first and second guides and oriented to extend substantially lengthwise along the surgical instrument and wherein said cable has an exposed surface between the first and second guides for providing illumination through said exposed surface;

an engaging surface associated with said second guide to frictionally and releasably secure the light cable to said second guide generally adjacent to one end portion of the cable; and a light source connected to the end portion of the cable opposite the end of the cable secured in the second guide.

* * * * *